(12) United States Patent
Nishiuchi

(10) Patent No.: US 9,381,378 B2
(45) Date of Patent: Jul. 5, 2016

(54) PARTICLE BEAM IRRADIATION SYSTEM AND METHOD FOR OPERATING THE SAME

(71) Applicant: HITACHI, LTD., Tokyo (JP)

(72) Inventor: Hideaki Nishiuchi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 143 days.

(21) Appl. No.: 14/163,143

(22) Filed: Jan. 24, 2014

(65) Prior Publication Data

US 2014/0296610 A1   Oct. 2, 2014

(30) Foreign Application Priority Data

Mar. 29, 2013   (JP) .................................. 2013-072563

(51) Int. Cl.
*A61N 5/10* (2006.01)
*H05H 13/04* (2006.01)
(52) U.S. Cl.
CPC ............. *A61N 5/1077* (2013.01); *H05H 13/04* (2013.01); *A61N 5/1043* (2013.01); *A61N 2005/1087* (2013.01); *H05H 2277/11* (2013.01)
(58) Field of Classification Search
None
See application file for complete search history.

(56) References Cited

U.S. PATENT DOCUMENTS

| 6,800,866 B2* | 10/2004 | Amemiya | G21K 5/04 250/396 R |
| 7,709,818 B2* | 5/2010 | Matsuda | A61N 5/1043 250/398 |
| 8,253,113 B2* | 8/2012 | Nishiuchi | A61N 5/10 250/396 R |
| 8,487,282 B2* | 7/2013 | Iseki | G01T 1/2935 250/397 |
| 8,766,217 B2* | 7/2014 | Balakin | G21K 1/087 250/492.3 |
| 8,841,638 B2* | 9/2014 | Hagino | A61N 5/1043 250/396 R |

(Continued)

FOREIGN PATENT DOCUMENTS

| JP | 2008-226740 A | 9/2008 |
| JP | 2011-124149 A | 6/2011 |
| JP | 4873563 B2 | 12/2011 |

OTHER PUBLICATIONS

Chu et al., "Instrumentation for treatment of cancer using proton and light-ion beams", Review of Scientific Instruments, Aug. 1993, pp. 2074-2093, vol. 64, No. 8.

(Continued)

*Primary Examiner* — Alexander H Taningco
*Assistant Examiner* — Nelson Correa
(74) *Attorney, Agent, or Firm* — Mattingly & Malur, PC

(57) ABSTRACT

Operation control data of each of the constituent sub-units of a synchrotron is constructed by a combination of module data items (initial acceleration data item, plural energy change data items, and a deceleration control data item), corresponding to plural control intervals, respectively. A control start value, a control completion value, and a computing function for connecting the control start value with the control completion value are expressed in each of module data items. Further, the plural module data items are corrected on the basis of a correction data item of a residual field, and a power-supply control command value is sequentially outputted. By preparing correction table data of the residual field, expressed by irradiation energy and irradiation stage numbers of the irradiation energy beforehand, the correction table data items of the plural module data items are selected from the correction table data to be prepared.

7 Claims, 10 Drawing Sheets

(56) References Cited

U.S. PATENT DOCUMENTS

| | | | | |
|---|---|---|---|---|
| 8,970,138 | B2* | 3/2015 | Nishiuchi | A61N 5/1067 250/396 ML |
| 9,067,066 | B2* | 6/2015 | Yamada | A61N 5/1048 |
| 2014/0021375 | A1* | 1/2014 | Nishiuchi | A61N 5/1077 250/492.3 |
| 2014/0152199 | A1* | 6/2014 | Arita | H05H 7/04 315/503 |
| 2015/0031931 | A1* | 1/2015 | Nishiuchi | A61N 5/1067 600/1 |
| 2015/0060703 | A1* | 3/2015 | Ogasawara | A61N 5/1048 250/492.3 |

OTHER PUBLICATIONS

Iwata et al., "Multiple-energy operation with extended flattops at HIMAC", Nuclear Instruments and Methods in Physics Research A 624, 2010, pp. 33-38.

Unpublished U.S. Appl. No. 13/945,041, filed Jul. 18, 2013.

Japanese Office Action received in corresponding Japanese Application No. 2013-072563 dated Aug. 4, 2015.

* cited by examiner

FIG.4A

| IRRADIATION-BEAM ENERGY $E_n$ | DEFLECTING MAGNETIC FIELD STRENGTH $B_n$ | EXCITING CURRENT $I_n$ | CORRECTION CURRENTS $\Delta I_{nm}$ IN RESPECTIVE IRRADIATION STAGES | | | | |
|---|---|---|---|---|---|---|---|
| | | | 1 | 2 | 3 | ... | m |
| $E_1$ | $B_1$ | $I_1$ | $\Delta I_{11}$ | $\Delta I_{12}$ | $\Delta I_{13}$ | ... | $\Delta I_{1m}$ |
| $E_2$ | $B_2$ | $I_2$ | $\Delta I_{21}$ | $\Delta I_{22}$ | $\Delta I_{23}$ | ... | $\Delta I_{2m}$ |
| $E_3$ | $B_3$ | $I_3$ | $\Delta I_{31}$ | $\Delta I_{32}$ | $\Delta I_{33}$ | ... | $\Delta I_{3m}$ |
| ⋮ | ⋮ | ⋮ | ⋮ | ⋮ | ⋮ | ... | ⋮ |
| $E_i$ | $B_i$ | $I_i$ | $\Delta I_{i1}$ | $\Delta I_{i2}$ | $\Delta I_{i3}$ | ... | $\Delta I_{im}$ |
| $E_j$ | $B_j$ | $I_j$ | $\Delta I_{j1}$ | $\Delta I_{j2}$ | $\Delta I_{j3}$ | ... | $\Delta I_{jm}$ |
| $E_k$ | $B_k$ | $I_k$ | $\Delta I_{k1}$ | $\Delta I_{k2}$ | $\Delta I_{k3}$ | ... | $\Delta I_{km}$ |
| ⋮ | ⋮ | ⋮ | ⋮ | ⋮ | ⋮ | ... | ⋮ |
| $E_n$ | $B_n$ | $I_n$ | $\Delta I_{n1}$ | $\Delta I_{n2}$ | $\Delta I_{n3}$ | ... | $\Delta I_{nm}$ |

| MODULE DATA ITEMS | NUMBER OF IRRADIATION STAGES m | CORRECTION CURRENT $\Delta I_s$ AT A CONTROL START VALUE | CORRECTION CURRENT $\Delta I_e$ AT A CONTROL COMPLETION VALUE |
|---|---|---|---|
| AC | 1 | - | $\Delta I_{i1}$ |
| $EC_{ij}$ | 2 | $\Delta I_{i1}$ | $\Delta I_{j2}$ |
| $EC_{jk}$ | 3 | $\Delta I_{j2}$ | $\Delta I_{k3}$ |
| DE | - | $\Delta I_{k3}$ | - |

403

| m | MODULE | $I_{start}$ | $I_{end}$ | $B(t)$ | Timing |
|---|---|---|---|---|---|
| 1 | AC | $I_{inj}$ | $I_i$ | $B_{AC}(t)$ | $T_{AC}$ |
| 2 | $EC_{ij}$ | $I_i$ | $I_j$ | $B_{EC\_ij}(t)$ | $T_{EC\_ij}$ |
| 3 | $EC_{jk}$ | $I_j$ | $I_k$ | $B_{EC\_jk}(t)$ | $T_{EC\_jk}$ |
| - | DE | $I_l$ | $I_{inj}$ | $B_{DE}(t)$ | $T_{DE}$ |

401a  402a  51

PARTICLE BEAM IRRADIATION SYSTEM AND METHOD FOR OPERATING THE SAME

BACKGROUND

The present invention relates to a particle beam irradiation system suitable for a particle-beam treatment making use of a charged particle beam (an ion beam) of a proton, a heavy ion, and so forth, and in particular, to a particle beam irradiation system capable of promptly realizing control of a change in beam-energy, and easily realizing reproducibility of the performance of an irradiation beam, and a method for operating the same.

A particle beam treatment whereby an affected part of a patient with a cancer is irradiated with an ion beam of a proton, or a heavy ion, and so forth, for treatment, has been well known as radiotherapy for a cancer. An ion beam irradiation method includes a scanning irradiation method as disclosed in "REVIEW OF SCIENTIC INSTRUMENTS", Vol. 64, No. 8, (August 1993), pp. 2074-2093.

In the case where a synchrotron is adopted as an ion beam generator for controlling a change in beam-energy, required in the scanning irradiation method, there is available a multistage extraction-control operation for realizing irradiation with plural ion beams differing in energy from each other, in one operation cycle inside the synchrotron, disclosed in Japanese Patent No. 4873563, Japanese Unexamined Patent Application Publication No. 2011-124149, and "Nuclear Instruments and Methods in Physics Research", No. A624, (September 2010), pp. 33-38, respectively, as a control method for realizing the control of a change in beam-energy.

SUMMARY

With the ion beam scanning method, the control of irradiation to an irradiation field (hereinafter referred to as a layer) in the direction of a depth of an affected part is realized by controlling the energy of an irradiation ion beam. For this reason, it is necessary to realize a change in the energy of an ion beam supplied from the ion beam generator in a short time in order to enhance a dose rate when the ion beam scanning method is applied. Further, with the ion beam scanning method, irradiation beam energy need be controlled according to magnitude of an affected part (a depth from a body surface), so that it is necessary to combine the irradiation beam energies together for respective patients as the objects of irradiation and for respective affected parts as the objects of irradiation to be thereby controlled.

In the case where the synchrotron is adopted as the ion beam generator, a series of operations such as injection, acceleration, extraction, and deceleration are controlled as one operation cycle. In the case where the control of a change in ion beam energy is repeatedly carried out as in the case of the scanning irradiation method, an operation cycle need be updated in a synchrotron, so that a problem has existed in that time for a change in energy is required. In Japanese Patent No. 4873563, Japanese Unexamined Patent Application Publication No. 2011-124149, and "Nuclear Instruments and Methods in Physics Research", No. A624, (September 2010), pp. 33-38, respectively, there is shown a multistage-extraction operation for extracting plural beams differing in energy from each other in one operation cycle, as a countermeasure against this problem.

For example, in "Nuclear Instruments and Methods in Physics Research", No. A624, (September 2010), pp. 33-38, operation-control data formed by integrating all energy-ranges that can be irradiated by the synchrotron is prepared, and a beam is extracted by extending a flat top by use of energy only for irradiation with the beam, thereby enabling an affected part to be irradiated with respective beams in all energies by one operation-control. Further, since the respective beams in all energies can be irradiated by the one operation-control, the synchrotron can always implement irradiation by use of the same operation-control data. Accordingly, the operation-control of the synchrotron in the particle beam irradiation system can be simplified, and in addition, a magnetic-field history of each of electromagnets making up the synchrotron can be always kept constant, so that there is obtained an advantageous effect of enhancing reproducibility of a range as well as positional accuracy of an irradiation beam.

However, in the case of forming an absorption dose range (Spread-Out Bragg Peak, hereinafter referred to as "SOBP") matching a thickness of the affected part by use of the operation-control data of the synchrotron shown in Japanese Patent No. 4873563, and "Nuclear Instruments and Methods in Physics Research", No. A624, (September 2010), pp. 33-38, respectively, there arises control time from an initial acceleration energy up to a relevant irradiation-starting energy as well as control time from an irradiation-completion energy up to a deceleration-starting energy, not directly contributing to irradiation with the beam. Under an irradiation condition in which SOBP is narrow, in particular, a ratio of the control time of an operation that does not directly contribute to the irradiation with the beam to an operation control time of the synchrotron will increase, so that a problem has existed in that a dose rate cannot be enhanced.

Further, in Japanese Unexamined Patent Application Publication No. 2011-124149, there is shown a control device of an accelerator having a magnetic-field reference generation unit for outputting information on magnetic flux density corresponding to elapsed time with reference to a coil current exciting a magnetic field coil of the accelerator, and a magnetic-field reference conversion unit for finding the coil current causing a magnetic-field corresponding to the information on the magnetic flux density to be generated. Then, there is shown a control method whereby the information on the magnetic flux density, outputted by the magnetic-field reference generation unit, is outputted through a combination of four types of patterns (an initial rise-pattern, a decrease-pattern, an increase-pattern, and a completion-pattern) to thereby realize the extraction of plural beams differing in energy from each other in one operation cycle. According to Japanese Unexamined Patent Application Publication No. 2011-124149, optional extraction of the plural beams differing in energy from each other can be executed by a combination of four types of magnetic flux densities in one operation cycle, so that irradiation-energy necessary for forming a predetermined SOBP can be optionally selected. For this reason, the control time of the operation, not directly contributing to the irradiation with the beam, representing a drawback in the case of Japanese Patent No. 4873563, and "Nuclear Instruments and Methods in Physics Research", No. A624, (September 2010), pp. 33-38, respectively, can be rendered shorter, and the dose rate can be enhanced.

However, if the optional extraction of the plural beams differing in energy from each other is executed through the combination of the four types of magnetic flux densities in one operation cycle, a magnetic-field history of electromagnets making up the synchrotron will not be kept constant. If the magnetic-field history is not kept constant, a slight misalignment against a current set value that is set in the power supply of the electromagnet occurs to a magnetic field generated in the electromagnet to thereby impair the reproducibility of a magnetic field generated against the current set value, so that the reproducibility of the range as well as the positional accuracy of the irradiation beam, as shown in Japanese Patent No. 4873563, and "Nuclear Instruments and Methods in Physics Research", No. A624, (September 2010), pp. 33-38, respectively, cannot be obtained, and therefore, it is difficult to achieve highly accurate reproduction of the range as well as the positional accuracy of the irradiation beam, as required by the particle beam irradiation system with the scanning irradiation method applied thereto. The same applies to electromagnets making up a beam transport unit for transporting a beam from the synchrotron to an irradiation unit.

It is therefore an object of the invention to provide a particle beam irradiation system capable of enhancing a dose rate, while securing reproducibility of a range as well as positional accuracy of an irradiation beam without relying on a combination of irradiation beam energies in a multistage extraction-control operation whereby the control of a change in the energy of the irradiation beam supplied from a synchrotron to an irradiation unit is realized in a short time.

To achieve the object described as above, with the present invention, the operation-control data of constituent sub-units of a synchrotron at the time of a multistage extraction-control operation is constructed by a combination of a plurality of module data items, corresponding to plural control intervals, respectively. Further, the plural module data items are corrected on the basis of correction data items of a residual field, and a power-supply control command value is sequentially outputted to the constituent sub-units of the synchrotron on the basis of the plural module data items as corrected. By preparing correction table data of the residual field, expressed by irradiation energy and irradiation stage numbers of the irradiation energy beforehand, the correction table data items of the plural module data items are selected from the correction table data to be prepared.

More specifically, the plural module data items making up the operation control data have a configuration including initial acceleration data AC for acceleration from an injection energy up to an irradiation energy in the initial stage according to an irradiation condition, plural energy change data items EC for acceleration or deceleration to the next irradiation energy, and a deceleration data item DE for completing beam-irradiation to decelerate down to the injection energy. These module data items each are made up of a control start value, a control completion value, and a computing function for connecting the control start value with the control completion value. Further, in order to secure reproducibility of a beam range as well as a beam position when the module data items are combined together according to the irradiation condition, a correction data item for correcting the control start value or the control completion value of the module data item is prepared for every module data items. As for the correction data item, a control-correction value expressed by an irradiation energy, and a stage number (in the present specification, referred to as an extraction-stage number where appropriate) emerging after an initial-acceleration control of the irradiation energy is prepared in a table data (in the present specification, referred to as correction table data where appropriate) in consideration of magnetic-field history at the time of the multistage extraction-control operation, and the correction data item corresponding to a combination of the module data items is selected from the correction table data to be prepared.

Thus, a multistage extraction-control capable of a flexible combination of irradiation energies is realized with the use of the operation control data constructed by a combination of the plural module data items, corresponding to plural control intervals, respectively. Further, after the module data item is corrected (that is, the control start value or the control completion value of the module data item is corrected) on the basis of the correction data item acquired from the correction table data expressed by the irradiation energy and the extraction-stage number of the irradiation energy, a control command value is sequentially outputted on the basis of the computing function, whereupon control of a change in the energy of an extraction beam of the synchrotron can be realized in a short time, and the reproducibility of a beam range as well as a beam position of an irradiation beam can be secured without relying on a combination of irradiation beam energies.

To be more specific, the present invention has the following feature.

A control device includes a supervision control unit that sets the irradiation condition on the basis of treatment planning information, an accelerator control unit that selects the operation control data as well as the correction data item of both the synchrotron and a beam transport unit, making up the particle beam irradiation system, on the basis of the irradiation condition, a power-supply control unit that outputs a control command value on the basis of the operation control data as well as the correction data item, selected by accelerator control unit, and a timing system that outputs timing signals for managing control-timing of the constituent units of the particle beam irradiation system. The control device further includes an interlock system that outputs an acceleration-start command for starting a beam-acceleration control in the synchrotron, an energy change command outputted on the basis of information on the course of irradiation with an ion beam irradiated to a patient, a deceleration control command for transition to the next operation cycle after the completion of a beam-extraction control within one operation cycle in the synchrotron, an extraction-control stop command for stopping beam-irradiation owing to abnormality, and so forth of a constituent unit of the particle beam irradiation system, and an irradiation-completion command for directing the completion of irradiation, and the timing system outputs the control timing signal on the basis of the acceleration-start command, the energy change command, and the deceleration control command, respectively.

In this connection, there is described hereinafter a method for correcting and sending out the control command value. As described in the foregoing, the module data items prepared in every control intervals are each made up of the control start value, the control completion value, and the computing function for connecting the control start value with the control completion value. In order to cause a beam to stably undergo acceleration, extraction, and deceleration, respectively, in the synchrotron, control values in respective intervals between the respective module data items of the operation control data need be continuously connected with each other. For this reason, a completion value of the initial acceleration data item need be coincided with the initial value of the energy change data item (that is, a control value at the time of a beam-extraction control. Similarly, if an irradiation-stage number when the irradiation energy in an initial acceleration control is defined as in the initial stage is "m", a completion value of the energy change data item in an m-th stage need be coincided with a start value of the energy change data item in an (m+1)-th stage, and a completion value of the energy change data item in the final stage need be coincided with a start value of the deceleration data item. For this reason, a relevant correction data item is selected according to the irradiation energy, and the irradiation-stage number m from the correction table data by the control-start value, and the control completion value of each of the module data items making up the operation control data, and the control-start value and the control completion value are corrected, respectively, by the correction data item. Thereafter, there is found derivative matching an arithmetic function (for example, linear function, polynomial function spline function, and so forth), where control values from a corrected control-start value up to a corrected control completion value are set in the module data item, whereupon a power-supply control command value is sequentially calculated by use of this derivative to be outputted. The module data item may be made up of either a physical amount of a magnetic field strength generated at a constituent unit as a candidate control target, and so forth, or a control amount of a current, voltage, and so forth, directly applied to a constituent unit as a candidate control target.

As described in the foregoing, in the case of correcting the control-start value as well as the control completion value of each of the module data items, a correction-control based on a magnetic-field history can be easily realized by finding derivative matching a predetermined function form to thereby execute sequential calculations on the basis of the derivative before sending out the correction data item.

Further, to achieve the object described as above, the operation control data is constructed by a combination of plural module data items (an initial acceleration data item, energy change data items, and a deceleration data item) corresponding to plural control intervals, respectively, in a beam transport unit for use in supplying a beam from the synchrotron to the irradiation unit, as well, and a control correction value selected from the correction table data of a magnetic-field history based on the irradiation energy, and the irradiation-stage number m is prepared as the correction data item, as is the case with the operation-control data of the constituent sub-units of a synchrotron. A control start value or a control completion value of each of the module data items making up the operation control data is corrected on the basis of the correction data item. A power-supply control command value generated from a corrected module data items is sequentially outputted to the constituent units of the beam transport unit.

With the present invention, in a multistage extraction-control operation capable of realizing a control of a change in the energy of an irradiation beam in a short time, a range as well as positional accuracy of the irradiation beam can be secured without relying on a combination of the respective energies of the irradiation beams.

Still further, with the present invention, beam irradiation in a desired energy range can be executed in a short operation cycle, and a dose rate can be enhanced to thereby shorten treatment time.

BRIEF DESCRIPTION OF THE DRAWINGS

FIG. 4A is a view showing correction table data corresponding to a magnetic-field history, according to the one embodiment of the invention;

FIG. 4B is a view showing a correction data item corresponding to the module data item, according to the one embodiment of the invention;

DETAILED DESCRIPTION

Embodiments of the invention are described hereinafter with reference to the accompanied drawings.

First Embodiment

Figure 1:
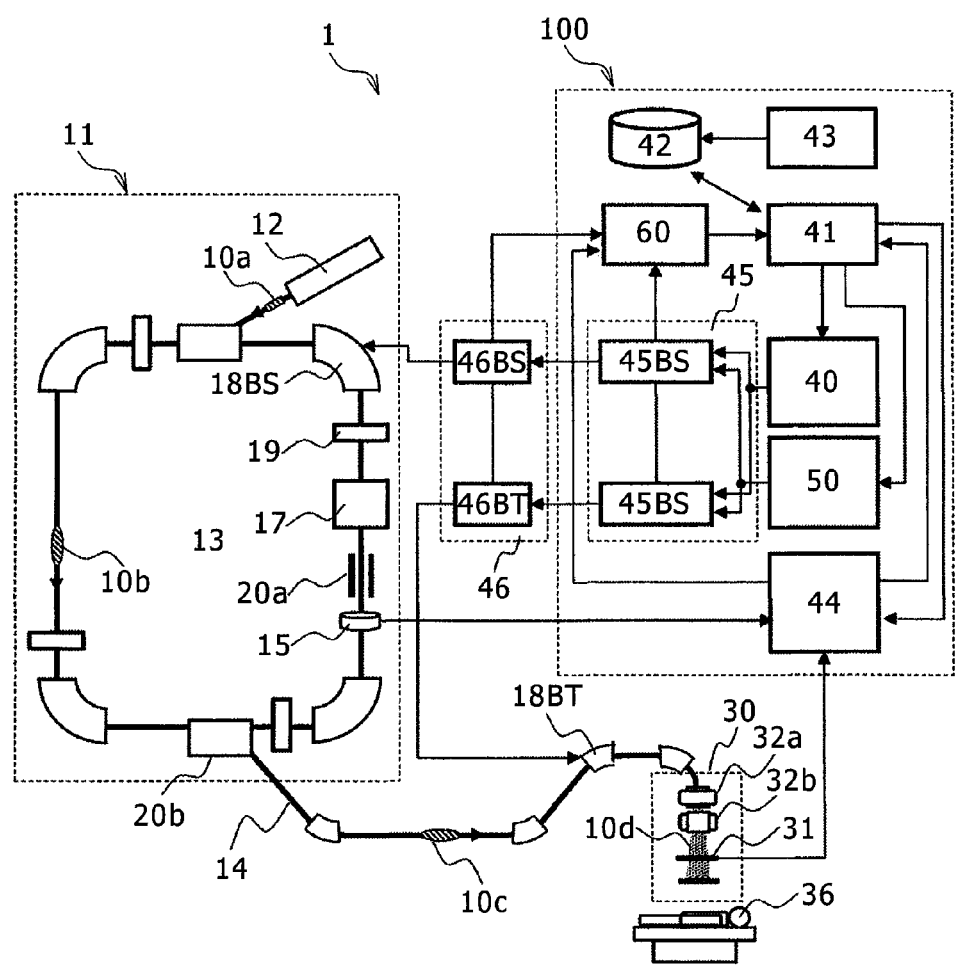
FIG. 1 is a view showing a configuration of one embodiment of a particle beam irradiation system according to the invention.

FIG. 1 is a view showing a configuration of a preferred embodiment of a particle beam irradiation system according to the invention. The particle beam irradiation system 1 according to the present embodiment includes an ion beam generator 11, a beam transport unit 14, and an irradiation unit 30. The ion beam generator 11 communicates with the irradiation unit 30 disposed in a treatment room via the beam transport unit 14.

The ion beam generator 11 includes an ion source (not shown), a preaccelerator 12, and a synchrotron 13. The ion source is connected to the preaccelerator 12, and the preaccelerator 12 is connected to the synchrotron 13. The preaccelerator 12 accelerates an ion beam 10 generated by the ion source up to energy capable of causing the ion beam 10 to be injected into the synchrotron 13. An ion beam 10a generated by the preaccelerator 12 is injected into the synchrotron 13.

The synchrotron 13 includes a radio-frequency accelerator (acceleration cavity) 17 for applying a radio-frequency voltage to an ion beam 10b revolving along an orbit to thereby accelerate the ion beam 10b up to a target energy, extraction radio-frequency electrodes 20a for causing the betatron-oscillation amplitude of a revolving ion beam to increase, and an extraction deflector 20b for taking out the revolving ion beam from the orbit.

The ion beam 10b injected into the synchrotron 13 is accelerated up to a desired energy upon energy being imparted thereto by the agency of an acceleration radio-frequency voltage applied to the radio-frequency acceleration cavity 17. At this point in time, the respective magnetic field strengths of a bending magnet 18BS, a quadrupole magnet 19, and so forth, and the frequency of the radio-frequency voltage applied to the radio-frequency acceleration cavity 17 are increased in conjunction with an increase in the revolving energy of the ion beam 10b such that the orbit of the ion beam 10b revolving inside the synchrotron 13 is kept constant.

With the ion beam 10b accelerated up to the desired energy, a condition under which the revolving ion beam 10b can be extracted (the stable critical condition of the revolving beam) is established by controlling the respective energization amounts of the quadrupole magnet 19, and a sextupole magnet (not shown) through an extracting-condition setting control. After completion of the extracting-condition setting control, an extraction radio-frequency voltage is applied to the extracting radio-frequency electrodes 20a to thereby cause an increase in the betatron oscillation amplitude of the beam 10b revolving in the synchrotron 13. Due to this increase in the betatron-oscillation amplitude, the revolving beam 10b having exceeded the stable critical-condition is extracted from the synchrotron 13 to the beam transport unit 14 via the extraction deflector 20b. The beam transport unit 14 stably transports the beam up to the irradiation unit 30 while deflecting the beam by use of a bending magnet 18BT. A control of beam-extracted from the synchrotron 13 can be realized at a high speed by controlling ON/OFF of the radio-frequency voltage applied to the extraction radio-frequency electrodes 20a.

After the completion of the control of beam-extracted from the synchrotron 13, the respective energization amounts of the quadrupole magnet 19, and the sextupole magnet (not shown) are controlled by an extracting-condition release-control, whereupon a release is made of the stable critical condition of the revolving beam 10b, formed at the time of setting the extracting condition.

After completion of the extracting-condition release control, the respective magnetic field strengths of the bending magnet 18, the quadrupole magnet 19, and so forth, and the frequency of the radio-frequency voltage applied to the radio-frequency acceleration cavity 17 are decreased, whereupon the ion beam 10b revolving inside the synchrotron 13 is decelerated, and the operation is shifted to the next operation cycle.

The irradiation unit 30 controls an ion beam 10c guided by the beam transport unit 14 so as to match to a depth from the body surface of a patient 36, and the shape of an affected part, thereby irradiating an affected part 37 of the patient 36 on a treatment bed with the ion beam 10c. A scanning irradiation method (refer to "REVIEW OF SCIENTIC INSTRUMENTS", Vol. 64, No. 8, (August 1993), p. 2086, FIG. 45) is available as an irradiation method, and the irradiation unit 30 adopts the scanning irradiation method. With the scanning irradiation method, the affected part 37 is directly irradiated with an ion beam 10d, and therefore, the ion beam 10d is high in utilization efficiency, so that the scanning irradiation method has a feature in that an irradiation can be executed with the ion beam 10d being more matched to the shape of an affected part than the case of a scatterer irradiation method according to the related art.

For adjustment of a beam range in the direction of a depth of an affected part, irradiation of a desired affected part is realized by changing the energy of an ion beam. In the case of the scanning irradiation method, in particular, the energy of the ion beam 10b revolving inside the synchrotron 13 is adjusted, and subsequently, the ion beam 10b is extracted to thereby cause an ion beam range to match to the depth of the affected part 37. For this reason, the control of a change in beam energy is required plural times during irradiation for treatment of the affected part. Further, as a method for beam irradiation in the direction of the plane of an affected-part, there are cited a spot-scanning irradiation method, and a raster scanning irradiation method, and so forth. In the case of the spot-scanning irradiation method, a surface of a plane of the irradiation of the affected-part is divided into dose-managing regions, called spots, scanning is stopped on a spot-by-spot basis to continue irradiation with the beam until a set irradiation-dose is reached, and subsequently the beam is stopped before shifting to the next irradiation spot position. Thus, the spot-scanning irradiation method is an irradiation method for updating an irradiation-start position on a spot-by-spot basis. Further, with the raster scanning irradiation method, the dose-managing region is set, as is the case with the spot-scanning irradiation method, however, scanning with a beam is not stopped on a spot-by-spot basis, and irradiation is executed while a scanning path is being scanned with the beam. Accordingly, uniformity of an irradiation dose is enhanced by execution of a repaint-irradiation whereby an irradiation dose per one irradiation is lowered, and the irradiation is repeated plural times.

Thus, the raster scanning irradiation method is an irradiation method for updating an irradiation-start position for each scanning path. Further, with the spot-scanning irradiation method as well, control may be exercised such that an irradiation dose per one irradiation, given against one spot position, is set low, and the plane of the irradiation as divided is scanned plural times, thereby reaching a final irradiation dose, as is the case with the raster scanning irradiation method.

Figure 2:
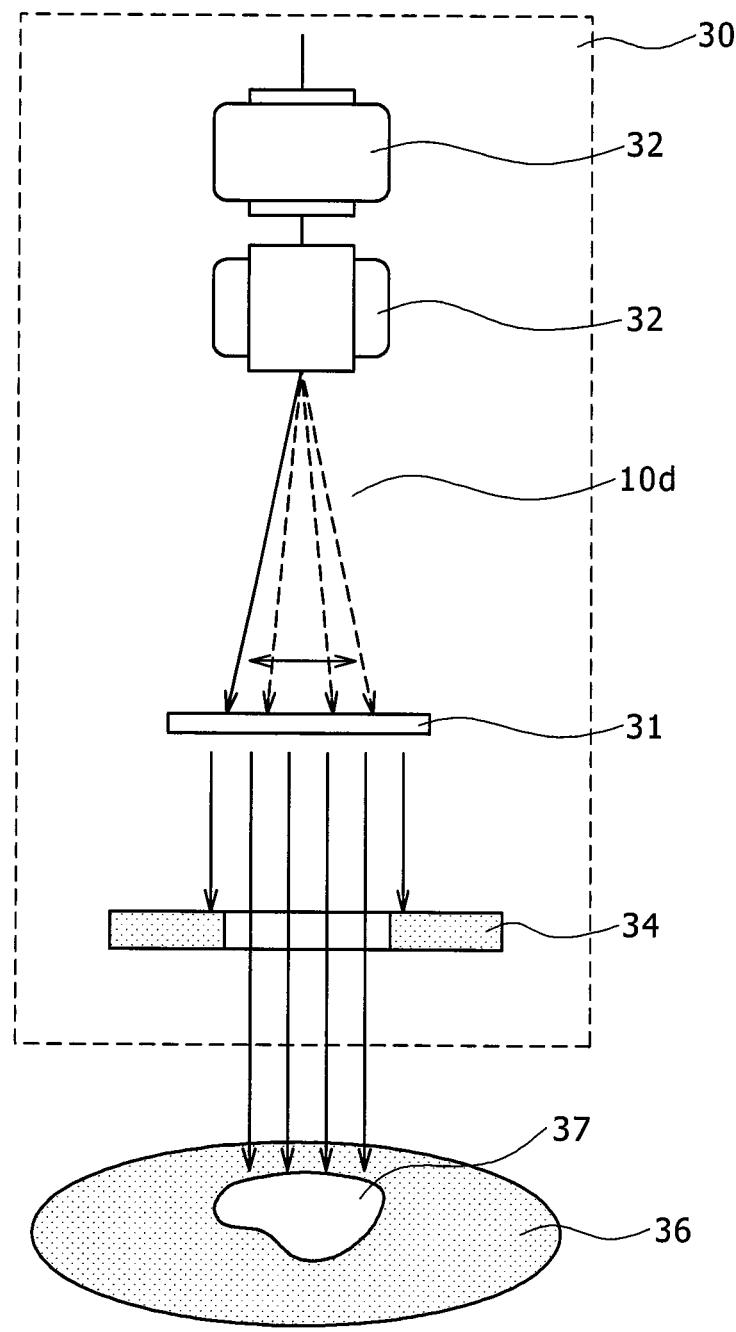
FIG. 2 is a view showing a configuration of an irradiation unit using a canning irradiation method, according to the one embodiment of the invention.

FIG. 2 shows a configuration of the irradiation unit 30. The irradiation unit 30 has scanning electromagnets 32a, 32b to cause a beam to scan the surface of a plane of an affected part so as to match the shape of the affected-part by use of the scanning electromagnets 32a, 32b. Further, the irradiation unit 30 has a dose monitor 31 for measuring an irradiation-dose of the ion beam 10d with which the patient is irradiated, and a beam-shape monitor (not shown), sequentially checking dose-intensity of the irradiation beam 10d, and a beam-shape, respectively, with the use of these constituent elements the irradiation unit 30. An irradiation field is formed by the beam 10d with which scanning is executed by the scanning electromagnets 32a, 32b in such a way as to match to the affected part 37 of the patient 36 by the agency of a collimator 34.

Reverting to FIG. 1, the particle beam irradiation system 1 according to the present embodiment includes a control system 100 (a control device). The control system 100 is made up of an accelerator control unit 40 for controlling the ion beam generator 11, and the beam transport unit 14, a supervision control unit 41 for supervising the particle beam irradiation system 1 in whole to be controlled, a treatment planning unit 43 for planning a beam irradiation condition applicable to a patient, a storage unit 42 for storing information planned by the treatment-panning unit 43, information and so forth, for controlling the synchrotron 13 serving as an ion beam generator, and the beam transport unit 14, an irradiation control unit 44 for controlling an irradiation dose of the ion beam 10d that is irradiated to constituent units of the irradiation unit 30, and the affected part 37, respectively, a timing system 50 for realizing a synchronized control of constituent sub-units of the synchrotron 13 as well as the beam transport unit 14, an interlock system 60 provided independently from the supervision control unit 41 in order to secure safety of the patient, and a power-supply control unit 45 for controlling a power supply unit 46 for respective constituent sub-units of the synchrotron 13 as well as the beam transport unit 14. The storage unit 42 serving as a part of the supervision control unit 41 may be provided in the supervision control unit 41.

The power supply unit 46 is a generic term for respective power supplies of the synchrotron 13, and the plural constituent sub-units of the beam transport unit 14. In FIG. 1, there are shown power supplies for plural sub-units, including a power supply unit 46BS as the power supply of the bending magnet 18BS of the synchrotron, and a power supply unit 46BT as the power supply of the bending magnet 18BT of the beam transport unit 14.

Similarly, the power-supply control unit 45 is a generic term for the plural power-control units corresponding to the plural power supplies 46, respectively, and in FIG. 1, there are shown a control unit 45BS of the power supply unit 46BS, and a control unit 45BT of the power supply unit 46BT.

Figures 11, 12:
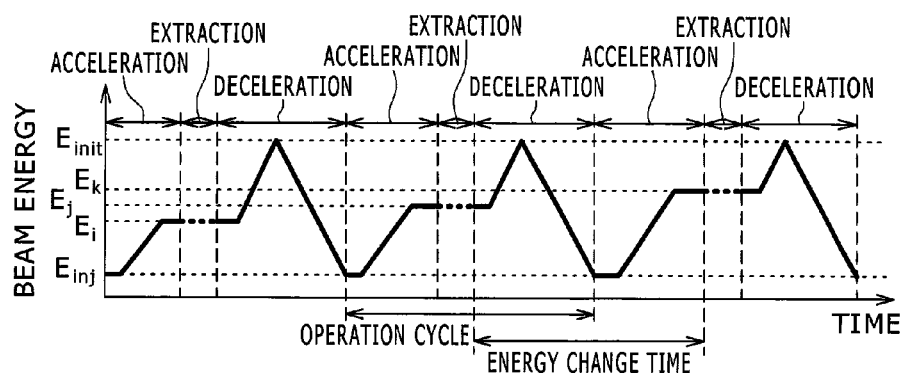
FIG. 11 is a view showing operation control data according to another embodiment of the invention, and a combination of module data items making up the operation control data.
FIG. 12 is a view showing an operation sequence of a synchrotron according to the related art.

Now, referring to the description of each cited literature, matters reviewed by the inventor, et al. are described hereinafter. FIG. 12 shows an operation sequence of the synchrotron 13 according to the related art. The synchrotron 13 executes a series of controls, such as acceleration, extraction, and deceleration, in one operation cycle.

In the case of the operation-control of the synchrotron 13 according to the related art, control data matched to a series of controls, as pattern data, is prepared in a memory of the power-supply control unit 45, and the power-supply control unit 45 used to sequentially update a control command value on the basis of a timing signal 52 outputted from the timing system 50 for managing control-timing of the respective constituent sub-units of the synchrotron 13.

The synchrotron 13 executes the control from acceleration up to deceleration in one operation cycle, as shown in FIG. 12, so that, in order to change the energy of the ion beam 10c to be extracted, an operation shifts to a deceleration control after the completion of an extraction-control to thereby cause a residual beam to decelerate, and subsequently, the operation cycle is updated. The control of a change to the desired energy is realized by updating the operation cycle to thereby accelerate the ion beam 10b again. Accordingly, with the operation-control of the synchrotron 13 according to the related art, time substantially equivalent to the one operation cycle is required as time necessary for a change to the energy of the ion beam 10b, resulting in longer treatment time, which has raised a problem from the standpoint of enhancement in dose rate.

The invention is concerned with a multistage extraction-control operation capable of realizing the control of a change in the energy of an irradiation beam in a short time, executed in a particle-beam irradiation system using a synchrotron, and it is possible to enhance a dose rate while a range as well as positional accuracy of each irradiation beam is secured without relying on a combination of the respective energies of irradiation beams to thereby shorten treatment time. The multistage extraction-control operation is described hereinafter in detail.

First, a structure of operation control data at the time of a multistage-extraction operation, as the feature of the present embodiment, is described with reference to FIGS. 3A and 3B.

Figure 3A:
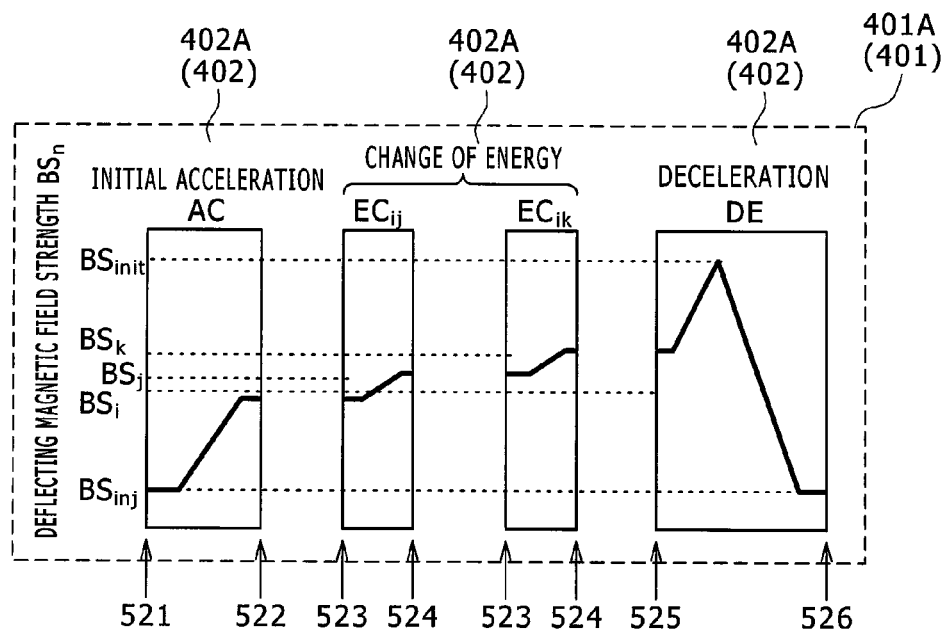
FIG. 3A is a view showing module data items making up operation control data of a synchrotron, as a constituent unit of the particle-beam irradiation system according to the one embodiment of the invention.
Figure 3B:
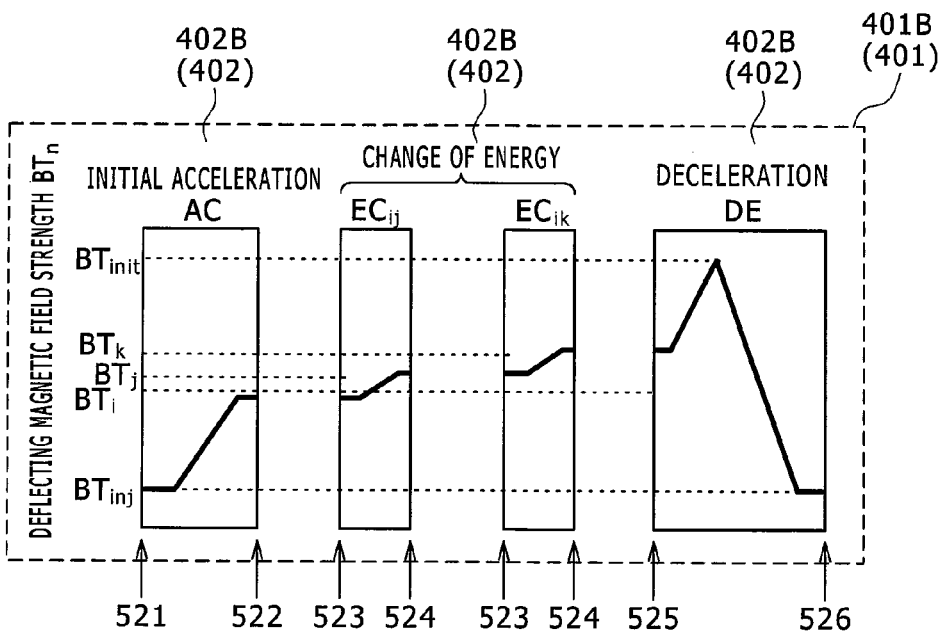
FIG. 3B is a view showing operation control data of a beam transport unit, as a constituent unit of the particle-beam irradiation system according to the one embodiment of the invention.

FIG. 3A is a view showing a configuration of operation control data 401A of the synchrotron 13, which is a constituent unit of the particle-beam irradiation system, as the feature of the present embodiment, and module data items 402A making up the operation control data 401A, and FIG. 3B is a view showing a configuration of operation control data 401B of the beam transport unit 14, a constituent unit of the particle-beam irradiation system, as the feature of the present embodiment, and module data items 402B making up the operation control data 401B. The module data items 402A, 402B each include data items such as an initial acceleration data item (AC), an energy change data item (EC), and a deceleration data item (DE). The operation control data 401A shows the control data of the bending magnet 18BS of the synchrotron 13, as the representative example of the control data of each of the hardware of the synchrotron 13, and the operation control data 401B shows the control data of the bending magnet 18BT of the beam transport unit 14, as the representative example of the control data of each of the hardware of the beam transport unit 14. Furthermore, the control data shows deflecting magnetic field strengths BS, BT, respectively. Because the deflecting magnetic field strength BS is controlled in sync with the deflecting magnetic field strength BT, the magnetic field strengths BS, BT are denoted as B for brevity in explanation in the following description. Further, in reality, there are prepared data items matching stage-numbers corresponding to the number of respective energies of irradiation beams, as shown in "Nuclear Instruments and Methods in Physics Research", No. A624, (September 2010), pp. 33-38; however, with the present embodiment, the data items that are present in three stages, respectively, are described. Still further, with the present embodiment, there is shown the operation control data for sequential irradiation with beams by starting from the beam low in energy toward the beam high in energy, however, even in the case of sequential irradiation with beams by starting from the beam high in energy toward the beam low in energy, the same advantageous effect can be obtained.

In the initial acceleration data item AC, a deflecting magnetic field strength Binj corresponding to an injection energy Einj is defined as a start-up value, and a deflecting magnetic field strength Bi corresponding to an irradiation energy Ei in the initial stage is defined as a completion value. The energy change data item EC is divided into ECij for causing an irradiation energy to change from Ei to Ej, and EC jk for causing the irradiation energy to change from Ej to Ek. ECij executes a control by use of a deflecting magnetic field strength Bj as the initial value, and a deflecting magnetic field strength Bk as a completion value, whereas ECjk executes a control by use of the deflecting magnetic field strength Bj as the initial value, and the deflecting magnetic field strength Bk as a completion value. In the deceleration data item DE, the deflecting magnetic field strength is enhanced from a control-start value Bk to an initialized magnetic field strength Binit in order to initialize the magnetic-field history of the bending magnet, and subsequently, the magnetic field strength is lowered to the injection magnetic field strength Binj A start-up as well as a completion of each of the module data items 402 is associated with the timing signal 52 outputted from the timing system 50. An acceleration-control start-timing signal 521 is allocated to a start-up point of the initial acceleration data item AC, and similarly, an acceleration-control completion-timing signal 522 is allocated to a completion point of the initial acceleration data item AC. An energy change control-start timing signal 523 is allocated to a start-up point of the energy change data item EC, and similarly, an energy change control completion timing signal 524 is allocated to a completion point of the energy change data item EC. Further, a deceleration control start-timing signal 525 is allocated to a start-up point of the deceleration data item DE, and similarly, a deceleration control completion-timing signal 526 is allocated to a completion point of the deceleration data item DE.

Now, the operation-control data shown in FIGS. 3A and 3B, respectively, has a configuration including one deceleration control data item DE corresponding to the energy Ek in the final stage, however, the operation-control data may have a configuration including the plural deceleration control data items DE corresponding to plural energies Ei, Ej, and Ek, respectively. Thus, if the deceleration control data items DE corresponding to the energies Ei, Ej, and Ek, respectively, are provided, this will enable the deflecting magnetic field strength to promptly shift from any of the energies to deceleration control, so that it is possible to realize updating of an operation cycle in a short time to thereby enhance a dose rat in the case of interrupting the irradiation with the ion beam.

Next, a structure of the correction table data 70 corresponding to a magnetic-field history, as the feature of the present embodiment, is described with reference to FIGS. 4A, 4B. FIG. 4A is a view showing the correction table data 70 corresponding to the magnetic-field history, as the feature of the present embodiment. In the correction table data 70, there is first shown an exciting current In (n=the number of energies that can be irradiated by the synchrotron) achieving a deflecting magnetic field strength Bn corresponding to an irradiation beam energy En. The exciting current In is preset on the basis of the excitation characteristics (I-B characteristics) of the bending magnet 18.

At the time of the multistage extraction-control operation, the irradiation beam energy En is divided into plural portions so as to be changed plural times in one operation cycle. Accordingly, the deflecting magnetic field strength B as well shifts to the deceleration control data item DE after the plural energy change data items EC are executed following the initial acceleration data item AC, as shown in FIGS. 3A and 3B, respectively. Let us review an exciting current for realizing the deflecting magnetic field strength in the second stage onwards in the case of an operation under such irradiation conditions described as above. For example, an exciting current value (Ij1) upon directly reaching Bj in the initial acceleration data item AC differs from an exciting current value (Ij2) at the magnetic field strength in the second stage, having once passed through the energy change data item ECij, in respect of a magnetic-field history, due to the presence or absence of a constant excitation interval (an interval of AC-ECij), so that a slight deviation occurs to the deflecting magnetic field strength Bj generated in the bending magnet even if the same exciting current Ij is set, and in consequence, correction of the exciting current is required. In the case of the multistage extraction-control operation, the reproducibility of a beam range as well as a beam position is required whatever magnetic-field history may be passed through, and therefore, the deflecting magnetic field strength Bj need be outputted with high reproducibility. For this reason, a correction current ΔInm (m=an irradiation-stage number when an irradiation energy in an initial acceleration control is defined as in the initial stage) is prepared for every irradiation stages beforehand, as the correction table data 70.

For example, an exciting current necessary for realizing the deflecting magnetic field strength Bj shown in FIGS. 3A and 3B, respectively, will be Ij+ΔIij2. The correction described as above is the correction of a completion value of the energy change data item ECij, and similarly, the correction of a start-up value of the energy change data item ECij will be Ii+ΔIi1.

For generalization of the correction of an exciting current, a control-start current value (Istart) of the energy change data item EC is expressed by the following formula (1):

$$I_{start}=I(B_{start})+\Delta I_s=I_n+\Delta I_{nm} \tag{1}$$

In the formula (1), In denotes an exciting current corresponding to energy En irradiated prior to an energy change control, and the ΔInm denotes a correction current corresponding to the stage number m of the exciting current In when the irradiation energy in the initial acceleration control is in the initial stage. Similarly, a control completion current value (Iend) of the energy change data item EC is expressed by the following formula (2):

$$I_{end}=I(B_{end})+\Delta I_e=I_{n+1}+\Delta I_{(n+1),(m+1)} \tag{2}$$

In the formula (2), I (n+1) denotes an exciting current corresponding to the next energy E (n+1) irradiated after the energy change control, and ΔI (n+1), (m+1) denotes a correction current corresponding to an irradiation stage number (m+1) where the exciting current I (n+1) is excited.

FIG. 4B shows a correction data item 403 corresponding to a combination of the module data items 402 shown in FIGS. 3A and 3B, respectively. In the correction data item 403, there are shown irradiation-stage number m, correction current values (ΔIs, ΔIe) corresponding to the control start-up value, and the control completion value, respectively, with reference to each module data block 402. It is necessary to continuously control the exciting current I between the correction current value (ΔIe) corresponding to the control completion value of the initial acceleration data item AC and the correction current value (ΔIs) corresponding to the control-start value of the energy change data item ECij, (an interval of AC-EC), between the correction current value (ΔIe) corresponding to the control completion value of the energy change data item ECij and the correction current value (ΔIs) corresponding to the control start value of the energy change data item ECjk (an interval of EC-EC), and between the correction current value (ΔIe) corresponding to the control completion value of the energy change data item ECjk and the correction current value (ΔIs) corresponding to the control-start value of the deceleration data item DE (an interval of EC-DE), respectively, so that the respective correction current values (ΔIs, ΔIe) are rendered identical in value to each other. Further, a correction current value may be set with reference to the control-start value of the initial acceleration data item AC, and the control completion value of the deceleration data item DE, respectively. However, with the present embodiment, the electromagnet is initialized in deceleration data item DE, and therefore, inputting of the current value can be dispensed with. In the execution of an actual control, the correction data item 403 corresponding to the module data item 402 can be easily selected by updating an irradiation-stage number counter (mi) to match the updating of a control-module, while referring to the correction current values (ΔIs, ΔIe) where an irradiation-stage number counter value (mi) coincides with the irradiation-stage number (m).

Figure 5:
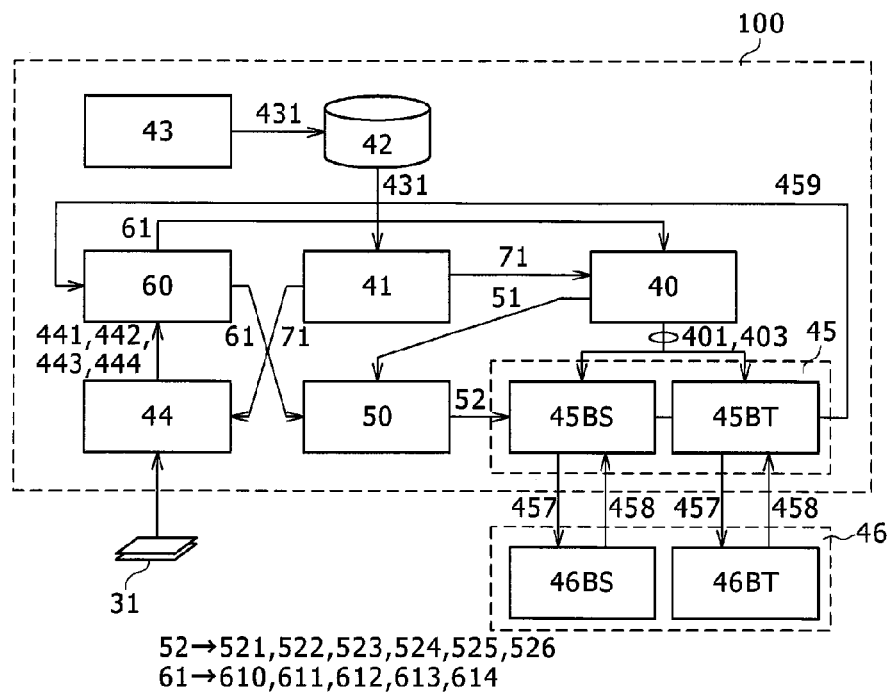
FIG. 5 is a view showing a configuration of a control system (a control device) for realizing a multistage extraction operation according to the one embodiment of the invention, and information-transmission among respective constituents units of the control system.
Figure 6:
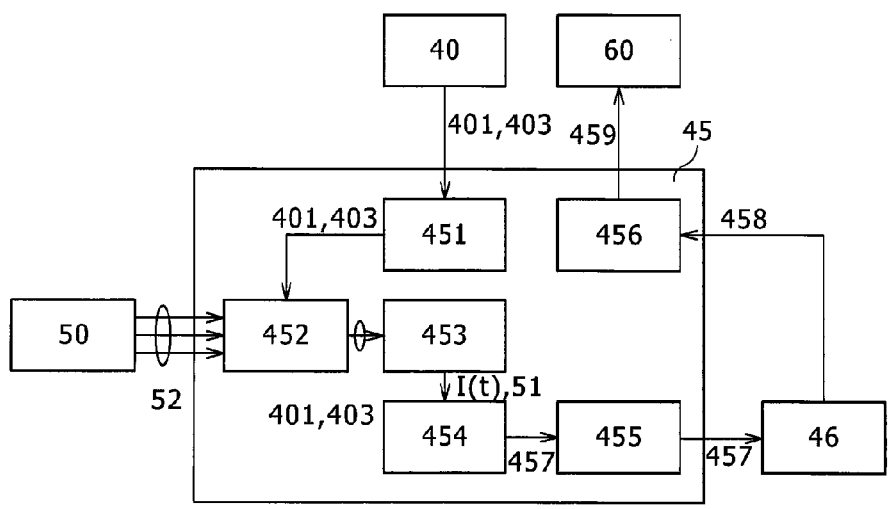
FIG. 6 is a view showing a configuration of a power-supply control unit according to the one embodiment of the invention.

Next, a configuration of the control system, information transmission among respective constituents units of the control system, and information are described with reference to FIGS. 5 through 7B. FIG. 5 is a view showing the configuration of the control system 100 (the control device) for realizing the multistage extraction operation as the feature of the present embodiment, and the information transmission among the respective units of the control system. FIG. 6 is a view showing a configuration of the power-supply control unit as the feature of the present embodiment. Further, FIG. 7A is a view showing an irradiation condition according to the one embodiment of the invention, and FIG. 7B is a view showing a combination of the module data items 402 making up the operation control data 401, and module control time 51 at which the module data item 402 is outputted.

The configuration of the control system 100 (the control device) for realizing the multistage-extraction-control operation as the feature of the present embodiment, and the information-transmission among the respective constituents units of the control system are described hereinafter with reference to FIG. 5. The control device is made up of the treatment planning unit 43 that outputs treatment planning information 431 on a patient, the storage unit 42 for holding the treatment planning information 431 outputted by the treatment-panning unit 43, the supervision control unit 41 for supervising the particle beam irradiation system so as to be controlled, the accelerator control unit 40 for controlling constituent sub-units of the ion beam generator 11 as well as the beam transport unit 14 in a supervising manner, the irradiation control unit 44 for controlling beam-irradiation directed to an affected part, the power-supply control unit 45 for individually controlling power supplies 46 of the synchrotron 13 as well as the constituent sub-units of the beam transport unit 14, the timing system 50 for managing control sequence as well as control-operation timing of the particle beam irradiation system, and the interlock system 60 for supervising an interlock-control with respect to beam-irradiation in the particle beam irradiation system. Herein, the power-supply control unit 45 shows the power-supply control unit 45BS for the bending magnets making up the synchrotron 13, and the power-supply control unit control unit 45BT for the bending magnets making up the beam transport unit 14. The respective module data items 402 making up the operation control data 401, and the correction data item 403 for correcting the module data items 402 slightly differ in control value from each other, however, a specific control method is in common with the module data items 402, and the correction data item 403.

Figure 7A:
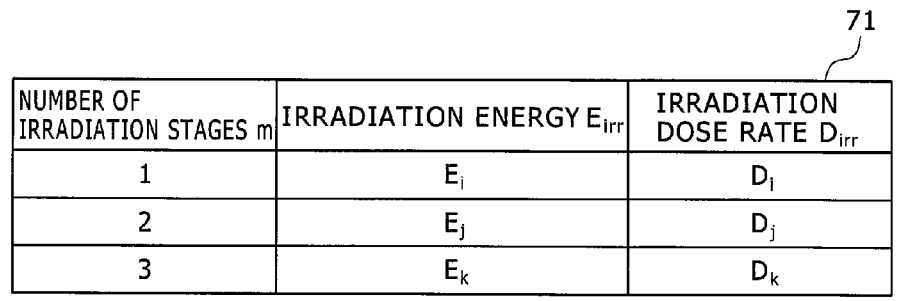
FIG. 7A is a view showing an irradiation condition according to the one embodiment of the invention.

The supervision control unit 41 sets an irradiation condition 71 made up of respective information pieces on the irradiation-stage number (m), irradiation energy (Eirr), irradiation dose (Dirr), and so forth, as shown in FIG. 7A, on the basis of the treatment planning information 431. The supervision control unit 41 transmits the irradiation condition 71 to the accelerator control unit 40, and the irradiation control unit 44, respectively. The accelerator control unit 40 selects the module data items 402 for use to be combined with each other on the basis of the irradiation condition 71, thereby constructing the operation control data 401 as shown in FIG. 7B. Now, a configuration of the operation control data 401 is described with reference to FIG. 7B.

Figure 7B:
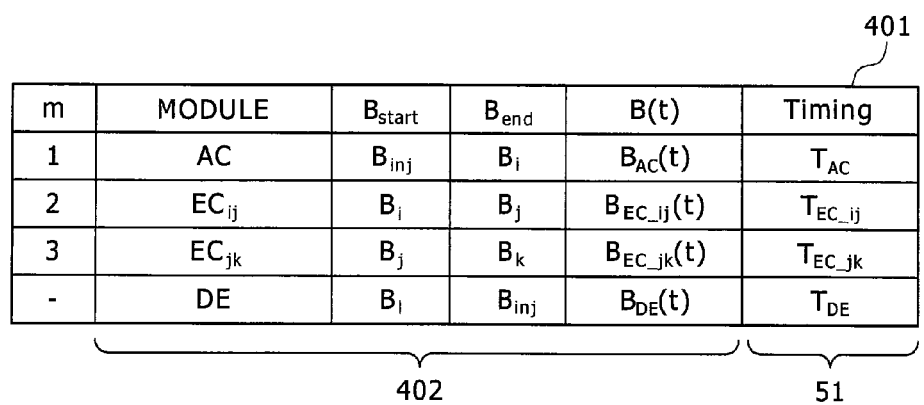
FIG. 7B is a view showing operation control data according to the one embodiment of the invention, and a combination of the module data items making up the operation control data.

The operation control data 401 is made up of the plural module data items 402 including one initial acceleration data item AC, plural energy change data items EC, and one deceleration data item DE, as shown in FIG. 7B, in accordance with the irradiation energy (Eirr), and the irradiation-stage number (m), shown in the irradiation condition 71, and module control time 51 showing control time in the module data item 402. Further, the module data item 402 is made up of a control start value (Bstart), a control completion value (Bend), and a computing function {B (t)} for connecting the control start value with the control completion value, with reference to the module data item. The control time (T) of each of the module data items 402 is described in the module control time 51. With the power-supply control unit 45, a control is started upon inputting of the timing signal 52 corresponding to each of the module data items 402, and subsequently, the control completion value of each of the module data items 402 is held at a given value to be sent after the elapse of the control time (T) to be in a standby state for inputting of the next timing signal 52. The accelerator control unit 40 transmits the operation control data 401 including these module data items 402, and the module control time 51 to the power-supply control unit 45. Furthermore, the accelerator control unit 40 extracts the module control time 51 from the operation control data 401 to be transmitted to the timing system 50. Further, the accelerator control unit 40 extracts a relevant correction data item 403 shown in FIG. 4B from the correction table data 70 shown in FIG. 4A on the basis of the module data items 402 making up the operation control data 401 to be transmitted so as to match the power-supply control unit 45.

The accelerator control unit 40 pre-stores a multitude of the initial acceleration data items AC, the deceleration control data items DE, and the deceleration data items DE, as the module data items 402 constructing the operation control data 401, in an energy range that can be irradiated by the synchrotron, and those data items corresponding to each other according to the irradiation condition 71 are selected from these control data items to be combined with each other, thereby flexibly realizing the construction of the operation-control data 401. Meanwhile, with the correction data, the module data items 402 differ in correction amount from each other depending on the module data item 402 in use, and the irradiation-stage number m, according to the irradiation condition 71. Accordingly, the accelerator control unit 40 stores the correction table data 70 of FIG. 4A, in a memory, and extracts a relevant correction data item 403 from the correction table data 70 according to a combination of the module data items 402 constructing the operation control data 401 to construct the correction data item 403, thereby realizing correction-control flexibly corresponding to the irradiation condition 71.

The power supply unit 46 is coupled to the power-supply control unit 45, and an irradiation beam monitor, such as the dose monitor 31, and so forth, and a scanning electromagnet power supply (nor shown) are coupled to the irradiation control unit 44.

The interlock system 60 supervises the interlock-control of the particle beam irradiation system 1, and receives control-request signals (441 to 444) transmitted from the irradiation control unit 44, and a power-supply control-subunit state signal 459 transmitted from the power-supply control unit 45, thereby sending out an interlock signal 61 on the basis of these control-request signals and the subunit state signal. The interlock signal 61 includes an acceleration-start command 610 for starting a beam-acceleration control in the synchrotron 13, an energy change command 611 generated on the basis of information on the course of irradiation with an ion beam irradiated to a patient, a deceleration control command 612 for transition to the next operation cycle after the completion of a beam-extraction control within one operation cycle in the synchrotron 13, an irradiation-completion command 613 for indicating the completion of irradiation, an extraction-control stop command 614 for stopping beam-irradiation owing to abnormality, and so forth. If the control-subunit state signal is normal when the control-request signal from the irradiation control unit 44 is received, these command signals are outputted as a control signal to the timing system 50, and the accelerator control unit 40, respectively. Further, the acceleration-command signal 610 for starting the beam-acceleration control in the synchrotron 13 may be outputted from the supervision control unit 41.

The timing system 50 outputs an acceleration-control start timing signal 521, an energy change control-start timing signal 523, and a deceleration-control start-timing signal 525, respectively, on the basis of the acceleration-start command signal 610 outputted from the supervision control unit 41 or the interlock system 60, the energy change command 611 outputted from the interlock system 60, and the deceleration control command 612.

A configuration of the power-supply control unit 45, as the feature of the invention, is described hereinafter with reference to FIG. 6. The power-supply control unit 45 is made up of a memory 451 for storing the module data items 402 making up the operation control data 401, together with the module control time 51, a sequence control circuit 452 for changing over the module data item 402, and the correction data item 403 on the basis of the timing signal 52 received from the timing system 50, an exciting-current function arithmetic circuit 453 for correcting a start-up value (Bstart) as well as a completion value (Bend) of the module data item 402 on the basis of the correction data item 403, and deriving an exciting-current function {I (t)} on the basis of the computing function {B (t)} set in the module data item 402, a control-current arithmetic circuit 454 for sequentially calculating a control current value on the basis of the exciting-current function {I (t)} derived in the exciting-current function arithmetic circuit 453, a control-current output circuit 455 for causing a control current value 457 outputted from the control-current arithmetic circuit 454 to be set in the power supply unit 46, and a subunit-state monitoring circuit 456 for receiving a subunit-state signal 458 from the power supply unit 46.

First, the operation control data 401 including the module data items 402, and the module control time 51, together with the correction data item 403, are transmitted from the accelerator control unit 40 to the power-supply control unit 45. The power-supply control unit 45 stores the operation control data 401 including the module data items 402, and the module control time 51, together with the correction data item 403, in the memory 451.

The sequence control circuit 452 receives the timing signal 52 outputted from the timing system 50 to read the module data item 402 and the module control time 51, corresponding to the timing signal 52, from the memory 451. More specifically, the sequence control circuit 452 reads the initial acceleration data item AC, and TAC indicating acceleration control-time, upon the acceleration-control start-timing signal 521 being inputted, and reads the energy change data item EC, and TEC indicating energy change control-time, upon the energy change control-start timing signal 523 being inputted, thereby selecting the deceleration data item DE and TDE indicating deceleration control-time, upon the deceleration control start-timing signal 525 being inputted. In this case, since the plural energy change data items EC have been prepared, the irradiation-stage number counter (mi) is provided in the sequence control circuit 452, and selection is made on the basis of the irradiation-stage number counter value. The irradiation-stage number counter (mi) executes initialization (mi=0) upon the acceleration-control start-timing signal 521 being inputted, executing addition (mi=1) when the acceleration-control completion-timing signal 522 is inputted. Similarly, upon the energy change control-start timing signal 523 being imputted, addition is made to the irradiation-stage number counter (mi=mi+1) and subsequently, a final update value (mi) of the irradiation-stage number counter is compared with the irradiation-stage number (mi) whereupon an energy change data item EC in which the final update value of the irradiation-stage number counter coincides with the irradiation-stage number (mi=m), and the energy change control-time TEC are selected.

The exciting-current function arithmetic circuit 453 converts the start-up value (Bstart) as well as the completion value (Bend) of the module data item 402 into exciting current values {I (Bstart)}, and {I (Bend)}, respectively, on the basis of the I-B characteristics, and these exciting current values are corrected by arithmetic expression, as shown in the formula (1) and the formula (2), respectively, into the correction data item 403 (ΔIs, ΔIe) to thereby find a start-up value (Istart) as well as a completion value (Iend) of the exciting current. Thereafter, there is derived the exciting-current function I (t) for connecting the start-up value (Istart) of the exciting current with the completion value (Iend) thereof so as to match an arithmetic function form (linear function, polynomial function, spline function, and so forth) of the computing function {B (t)} shown in the module data item 402.

The control-current arithmetic circuit 454 reads coefficients of respective degrees expressing the exciting-current function {I (t)} derived in the exciting-current function arithmetic circuit 453, together with the module control time 51 during a control interval, to sequentially calculate the control current value 457 at a given time-interval, thereby sending out the control current value 457 to the control-current output circuit 455. In this case, if updated output-time of the control current value 457 has reached the control time shown in the module control time 51, the control-current arithmetic circuit 454 holds a calculation result (a final updated result) obtained upon the control time being reached to be outputted. By application of an updating-control function described as above, emission of the control current value 457 at a given value can be realized when a beam-extraction control is executed. The control-current output circuit 455 outputs the control current value 457 to the power supply unit 46 on the basis of the module control time 51.

The power supply unit 46 executes an excitation-control based on the control current value 457 outputted from the power-supply control unit 45. On the other hand, the power supply unit 46 sequentially transmits loads of the electromagnets coupled thereto, and so forth, and the subunit-state signal 458 of the power supply unit itself to the power-supply control unit 45. The power-supply control unit 45 transmits the state-signal of the power-supply control unit 45, together with the constituent-unit state signals of the power supply unit proper and the loads thereof, as the power-supply control-unit state signal 459, to the interlock system 60.

Figure 8:
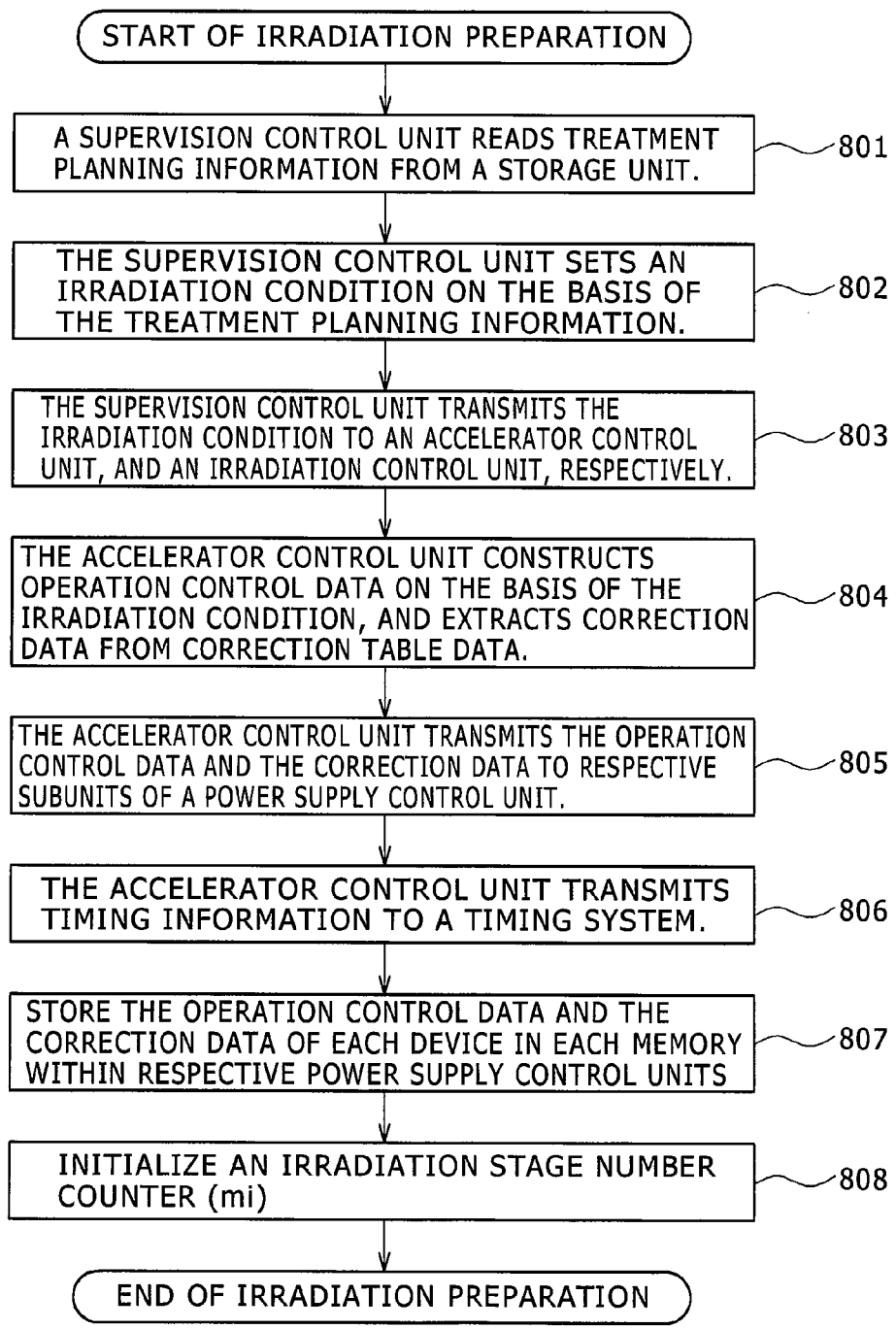
FIG. 8 is a view showing a flow of irradiation-preparation made prior to starting up the multistage extraction operation according to the one embodiment of the invention.

Referring to FIG. 8, an irradiation-preparation procedure is described hereinafter. First, the treatment planning unit 43 stores (not shown) the treatment planning information 431 including a beam range, a SOBP width, an irradiation-dose, and so forth, necessary for the irradiation of a patient, in the storage unit 42.

The supervision control unit 41 reads the treatment planning information 431 from the storage unit 42 (step 801). The supervision control unit 41 sets the irradiation condition 71 including the irradiation energy (Eirr), the irradiation-stage number (m), and the irradiation dose (Dirr), and so forth, actually adopted by the accelerator control unit 40, and the irradiation control unit 44, respectively, on the basis of the treatment planning information 431 (step 802). The supervision control unit 41 transmits the irradiation condition 71 to the accelerator control unit 40, and the irradiation control unit 44, respectively (step 803). The accelerator control unit 40 extracts the module data items 402 as well as the module control time 51, corresponding to the irradiation condition 71, to be combined in the order of irradiation to thereby construct the operation control data 401, and extract the correction data item 403 corresponding to the irradiation condition 71, from the correction table data 70 (step 804), before transmitting the operation control data 401 and the correction data item 403 to the respective sub-units of the power-supply control unit 45 (step 805). Further, the accelerator control unit 40 transmits the module control time 51 extracted from the operation control data 401 to the timing system 50 (step 806). The power-supply control unit 45 stores the operation control data 401 (the module data items 402 and module control time 51) and the correction data item 403 in the memory 451 so as to match the stage number m (step 807).

Finally, the irradiation-stage number counter (m) in use when reference is made to the correction data item 403 of the power-supply control unit 45 is initialized (step 808).

Figure 9:
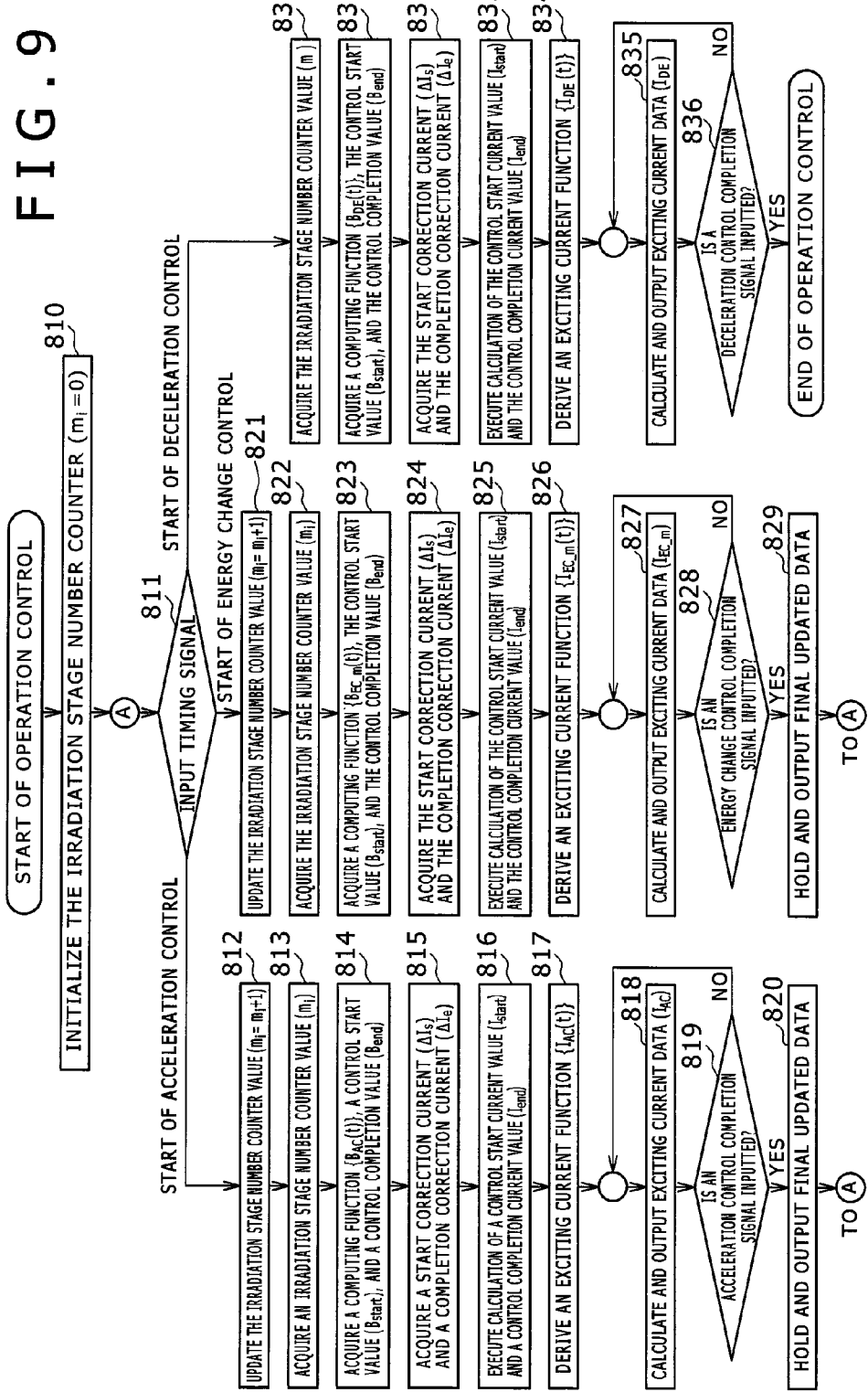
FIG. 9 is a view showing a flow of an operation-control at the time of execution of the multistage extraction operation according to the one embodiment of the invention.

An operation-control sequence of the particle beam irradiation system is described with reference to FIG. 9. Upon an operation-start command being transmitted from an operator (not shown), the particle beam irradiation system starts an operation-control. At the start of the operation-control, the power-supply control unit 45 initializes the irradiation-stage number counter (m) in order to select a correction data item 403 (step 810). Thereafter, the power-supply control unit 45 shifts to a standby state for inputting of the timing signal 52 transmitted from the timing system 50 (step 811). A control henceforth is executed on the basis of the timing signal 52 as inputted.

A control sequence in the case of the timing signal 52 being the acceleration-control start-timing signal 521 is shown hereinafter. First, the irradiation stage number counter (mi) is updated {mi=(mi+1)}(step 812), and thereafter, an irradiation-stage number counter value (mi) is acquired (step 813). The initial acceleration data item AC is selected from the operation control data 401 to thereby acquire the computing function {Bac (t)}, the control start value (Bstart), and the control completion value (Bend) (step 814). Next, respective correction current values (ΔIs, ΔIe) coinciding with the stage number m of the correction data item 403 coinciding with irradiation-stage number counter value (mi) are acquired (step 815), whereupon the control-start current value (Istart) and the control completion current value (Iend) are calculated from the control start value (Bstart), the control completion value (Bend), and the respective correction current values (ΔIs, ΔIe) on the basis of the formula (1), and the formula (2) (step 816), and an exciting-current function {Iac (t)} is derived on the basis of the computing function {Bac (t)} of the initial acceleration data item AC (step 817). In this case, the correction current value corresponding to the initial acceleration data item AC will be only the correction current value (ΔIe) at the time of control completion. An exciting current data item (Iac) is calculated on the basis of the exciting-current function {Iac (t)} as derived to be outputted until the acceleration-control completion-timing signal 522 is inputted (step 818). If the acceleration-control completion-timing signal 522 is inputted (step 819), the operation-control holds a final updated data item of the exciting current data item (Iac) to be outputted, thereby reverting to a flow for determination on the input-timing signal (sep 820). Further, description is omitted in a flow chart shown in FIG. 9, however, with respect to the ion beam 10b accelerated henceforth up to the desired energy, the condition under which the revolving ion beam 10b can be extracted (the stable critical-condition of the revolving beam) is established by controlling the respective energization amounts of the quadrupole magnet 19, and the sextupole magnet (not shown) through the extracting-condition setting control. After the completion of the extracting-condition setting control, an extraction radio-frequency voltage is applied to the extraction radio-frequency electrodes 20a to thereby cause an increase in the betatron-oscillation amplitude of the beam 10b revolving in the synchrotron 13. Due to this increase in the betatron-oscillation amplitude, the revolving beam 10b having exceeded the stable critical-condition is extracted from the synchrotron 13 to the beam transport unit 14 via the extraction deflector 20b. The beam transport unit 14 stably transports the beam up to the irradiation unit 30 while deflecting the beam by use of the bending magnet 18BT. The extracting-condition release-control is executed after completion of the control of the beam-extracted from the synchrotron 13, and subsequently, the timing signal 52 directing the next operation-control is inputted.

If the energy change control-start timing signal 523 or the deceleration control start-timing signal 525 is inputted in the determination on the input-timing signal (the step 811), the main control sequence is substantially identical to that in the case of the acceleration-control start-timing signal 521 being inputted, however, the respective correction current values (ΔIs, ΔIe) at the control start-up time, and at the control completion time, as the respective correction current values corresponding to the energy change module EC, are acquired (steps 824, 825), and the correction current value (ΔIs) at the control-start time, as the correction current value corresponding to the deceleration module DE, is acquired (steps 832, 833).

Upon the deceleration control completion-timing signal 526 being inputted after execution of the control sequence described as above, an operation-control is completed.

Figure 10A:
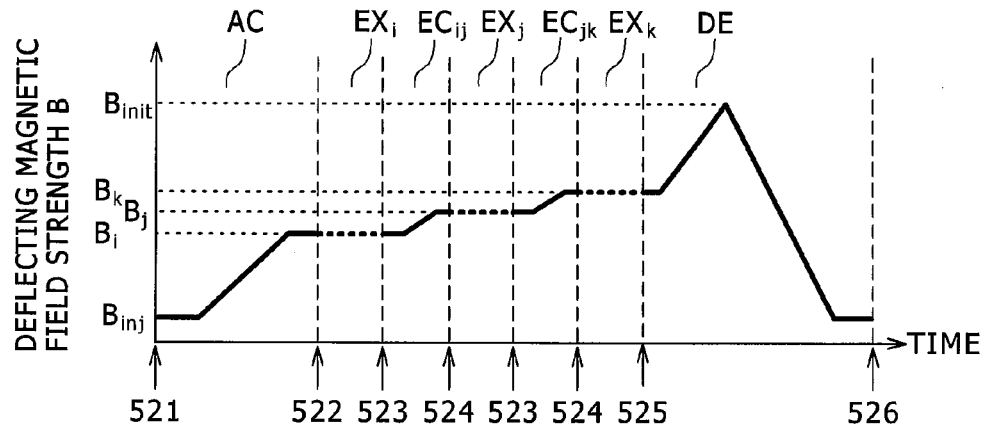
FIG. 10A is view showing variation in deflecting magnetic field strength when the multistage extraction operation according to the one embodiment of the invention is carried out by combination of the module data items shown in FIG. 3A, 3B, respectively.

An electromagnet control sequence using the module data items 402 making up the operation control data 401, and the correction data item 403 based on the correction table data 70, as previously described, is described hereinafter with reference to FIGS. 10A, 10B. FIG. 10A shows variation in deflecting magnetic field strength B over time in the case of operating the synchrotron 13, and the beam transport unit 14, respectively, by combining the module data items shown in FIGS. 3A and 3B, respectively, with each other, and FIG. 10B shows variation in the exciting current I over time, for realizing the variation in the deflecting magnetic field strength B shown in FIG. 10A.

In consequence of the respective control timing signals 521 to 526 being inputted, the initial acceleration data item AC, the energy change data items ECij, EC jk, and the deceleration control module DE are sequentially selected and updated. Further, the beam-extraction control is executed between the respective control modules (EXi between AC and ECij, EXj between ECij and ECjk, and EXk between ECjk and DE), as shown in EXi to EXk, respectively. The final updated data of the control module is held and outputted in respective module-control intervals (depicted by a dotted line in the figure).

Figure 10B:
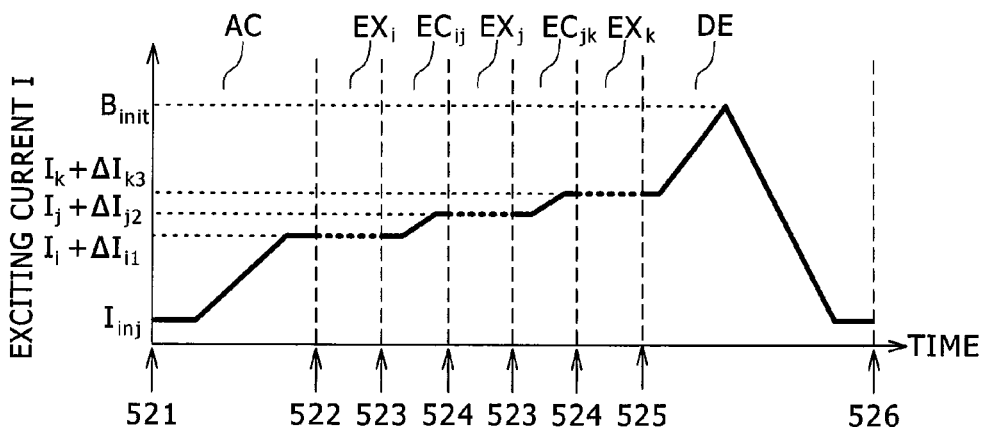
FIG. 10B is a view showing an exciting current value of an electromagnet, for realizing the variation in the deflecting magnetic field strength shown in FIG. 10A.

The control-start value of the exciting current I in the initial acceleration data item AC is at a current value Iinj at the time of an injection control, and a control completion value thereof will be a current Ii corresponding to Bi with a current-correction data ΔIi1 added thereto, that is, Ii+ΔIi1, as shown in FIG. 10B. The control-start value thereof in the energy change data item ECij is identical to the control completion value thereof in the initial acceleration data item AC, and a control completion value thereof will be a current IJ corresponding to BJ with a current-correction data ΔIj2 added thereto, that is, Ij+ΔIj2. Similarly, the control-start value thereof in the energy change data item ECjk is identical to the control completion value thereof in the energy change data item ECij, that is, Ij+ΔIj2, and the control completion value thereof will be a current Ik corresponding to Bk with a current-correction data Δk3 added thereto, that is, Ik+Δk3. Lastly, a control-start value thereof in the deceleration control module DE is Ik+Δk3, which is identical to the final updated-value of the energy change data item ECjk, and the control completion value thereof in the deceleration control module DE will be the current value Iinj at the time of the injection control, reached after the exciting current I is enhanced up to an initialization current value Iinit. Thus, in order to realize a deflecting magnetic field strength Bn corresponding to each irradiation energy, a predetermined deflecting magnetic field strength Bn can be stably outputted even against an optional combination of irradiation energies by correcting the control-start value or the control completion value of the exciting current In through the correction data item 403, thereby enabling the reproducibility of the beam range and the beam position in the multistage extract-control operation to be secured.

Second Embodiment

FIG. 11 is a view showing operation control data 401*a* according to another (a second) embodiment of the invention. A particle beam irradiation system according to the present embodiment is identical in hardware configuration to the particle beam irradiation system 1. In the case of the operation control data 401 according to the first embodiment, the control start value, the control completion value, and the computing function for connection therebetween with reference to each of the module data items 402 are the control start value (Bstart), the control completion value (Bend), and the computing function {B (t)}, with reference to the deflecting magnetic field strength Bn, respectively, whereas, with the present embodiment, the control start value, the control completion value, and the computing function with reference to each of the module data items 402*a* are set on the basis of a control current value In. More specifically, a means for executing an I-B conversion is prepared in the accelerator control unit 40 at the time of generation of each of the module data items 402*a*, and a control start value (Istart), a control completion value (Iend), and a computing function {I (t)}, respectively, with reference to each of the module data items 402*a*, are made up on the basis of results of the I-B conversion. If the module data items 402*a* is made up in such a way as described above, this will render it possible to eliminate the need for the exciting-current function arithmetic circuit 453 for use in subjecting the start-up value (Bstart), the completion value (Bend), and the computing function {B (t)}, respectively, with reference to the deflecting magnetic field strength Bn, to the I-B conversion within the power-supply control unit 45, so that loads of sequential processing by the power-supply control unit 45 can be reduced.

What is claimed is:

1. A particle beam irradiation system comprising:
    a synchrotron for accelerating an ion beam to be extracted;
    a beam transport unit for transporting the ion beam extracted from the synchrotron; and
    an irradiation unit for executing irradiation with the ion beam transported by the beam transport unit,
    wherein
    operation control data of constituent sub-units of the synchrotron and/or the beam transport unit is constructed by a combination of a plurality of module data items, corresponding to plural control intervals, respectively, and
    a control device is provided whereby the plural module data items are corrected by use of a correction data item acquired from correction table data,
    a power-supply control command value is sequentially outputted to the constituent sub-units of the synchrotron and/or the beam transport unit based on the plural module data items, as corrected,
    each of the plural module data items includes a control start value, a control completion value, and a computing function for connecting the control start value with the control completion value, and
    the control device corrects the control start value and the control completion value based on the correction data item, sequentially generating the control command value based on the control start value and the control completion value, as corrected, and the computing function, before being outputted.

2. The particle beam irradiation system according to claim 1, wherein the plural module data items each include an initial acceleration data item, a plurality of energy change data items, and a deceleration data item.

3. The particle beam irradiation system according to claim 1,
    wherein the control device includes:
        a supervision control unit that controls the particle beam irradiation system in a supervising manner;
        an accelerator control unit that controls the synchrotron and the beam transport unit in a supervising manner;
        a power-supply control unit that individually controls the synchrotron and respective constituent sub-units of the beam transport unit; and
        a timing system that outputs a plurality of control timing signals for managing control-timing of respective constituent units of the particle beam irradiation system,
    wherein the plural module data items making up the operation control data are stored in the accelerator control unit, the accelerator control unit constructs the operation control data by combination of the plural module data items making up the operation control data, and control-timing information on the plural module data items based on an irradiation condition set by the supervision control unit, concurrently selecting control-correction values corresponding to the plural module data items, respectively, as the correction data items, from the correction table data, to thereby set the operation control data and the correction data items in the power-supply control unit, and
    wherein the power-supply control unit receives the control timing signals outputted by the timing system to select a relevant module data item from among the plural module data items based on the control timing signals, correcting a selected module data item by use of the correction data item, thereby updating the power-supply control command value.

4. The particle beam irradiation system according to claim 3,
    wherein the control device further includes an interlock system that outputs:
        an acceleration-start command for starting a beam-acceleration control in the synchrotron,
        an energy change command outputted based on information on a course of irradiation with the ion beam irradiated to a patient,
        a deceleration control command for transition to a next operation cycle after completion of a beam-extraction control within one operation cycle in the synchrotron,
        an extraction-control stop command for stopping beam-irradiation owing to abnormality of a constituent unit of the particle beam irradiation system, and
        an irradiation-completion command for indicating the completion of irradiation, and
    wherein the timing system outputs the control timing signal based on the acceleration start command, the energy change command, and the deceleration control command outputted from the interlock system.

5. The particle beam irradiation system according to claim 3, wherein the accelerator control unit selects control-correction values corresponding to a control-start value and a control completion value, respectively, with reference to a module data block, prepared in the plural control intervals, as the correction data item, from the correction table data, thereby correcting the control-start value and the control completion value, respectively, based on the correction data item.

6. A method for operating a particle beam irradiation system having a synchrotron for accelerating an ion beam to be extracted, a beam transport unit for transporting the ion beam extracted from the synchrotron, and an irradiation unit for executing irradiation with the ion beam transported by the beam transport unit, the method comprising:
   constructing operation control data of constituent units of the particle beam irradiation system by a combination of a plurality of module data items corresponding to plural control-intervals, respectively;
   preparing a control-correction value expressed by irradiation energy, and a stage number emerging after an initial-acceleration control of the irradiation energy, in a correction table data, apart from the operation control data;
   selecting a correction data item, corresponding to the combination of the plural module data items, from correction table data so as to be readily available; and
   correcting the module data items based on the correction data item, and subsequently, combining the module data items with each other to thereby sequentially send out respective control command values of the constituent units of the particle beam irradiation system, wherein
      each of the plural module data items includes a control start value, a control completion value, and a computing function for connecting the control start value with the control completion value, and
      the control start value and the control completion value are corrected, respectively, based on the correction data item, and the control command value is sequentially generated based on the control start value and the control completion value, as corrected, and the computing function, before being outputted.

7. The method for operating the particle beam irradiation system, according to claim 6, wherein the plural module data items include an initial acceleration data item, a plurality of energy change data items for changing energy in order to extract respective ion beams in plural energies, and a deceleration data item.

* * * * *